(12) United States Patent
Parker

(10) Patent No.: US 8,465,536 B2
(45) Date of Patent: Jun. 18, 2013

(54) PROSTHESIS DEPLOYMENT SYSTEM

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2787 days.

(21) Appl. No.: 11/099,733

(22) Filed: Apr. 6, 2005

(65) Prior Publication Data

US 2005/0222664 A1    Oct. 6, 2005

Related U.S. Application Data

(60) Provisional application No. 60/559,764, filed on Apr. 6, 2004.

(51) Int. Cl.
*A61F 2/06*    (2006.01)

(52) U.S. Cl.
USPC ........................................................ 623/1.11

(58) Field of Classification Search
USPC ................................................ 623/1.11, 1.12
See application file for complete search history.

(56) References Cited

U.S. PATENT DOCUMENTS

| | | | |
|---|---|---|---|
| 4,055,187 A * | 10/1977 | Patel et al. | 604/103 |
| 4,562,596 A | 1/1986 | Kornberg | |
| 4,580,568 A | 4/1986 | Giaturco | |
| 4,665,918 A | 5/1987 | Garza et al. | |
| 4,950,227 A | 8/1990 | Savin et al. | |
| 5,387,235 A | 2/1995 | Chuter | |
| 5,480,423 A * | 1/1996 | Ravenscroft et al. | 623/1.11 |
| 5,603,698 A * | 2/1997 | Roberts et al. | 604/104 |
| 5,693,083 A | 12/1997 | Baker et al. | 623/1 |
| 5,693,086 A * | 12/1997 | Goicoechea et al. | 623/1.11 |
| 5,700,253 A | 12/1997 | Parker | |
| 5,720,776 A | 2/1998 | Chuter et al. | |
| 5,957,974 A * | 9/1999 | Thompson et al. | 623/1.13 |
| 6,206,931 B1 | 3/2001 | Cook et al. | |
| 6,287,329 B1* | 9/2001 | Duerig et al. | 623/1.11 |
| 6,613,075 B1* | 9/2003 | Healy et al. | 623/1.11 |
| 2001/0044629 A1* | 11/2001 | Stinson | 606/108 |
| 2001/0049547 A1* | 12/2001 | Moore | 623/1.11 |
| 2003/0233140 A1 | 12/2003 | Hartley et al. | |
| 2004/0054396 A1 | 3/2004 | Hartley et al. | |
| 2004/0098079 A1 | 5/2004 | Hartley et al. | |
| 2004/0193252 A1 | 9/2004 | Perez et al. | 623/1.23 |
| 2005/0049674 A1 | 3/2005 | Berra et al. | 623/1.13 |

FOREIGN PATENT DOCUMENTS

| | | |
|---|---|---|
| WO | WO 98/53761 A1 | 12/1998 |
| WO | WO 99/29262 A1 | 6/1999 |
| WO | WO 03/034948 A1 | 5/2003 |
| WO | WO 03/053287 A1 | 7/2003 |

* cited by examiner

*Primary Examiner* — Melanie Tyson
(74) *Attorney, Agent, or Firm* — Brinks Hofer Gilson & Lione

(57) ABSTRACT

A stent deployment system includes a handle and a flexible sheath coupled the handle. A flexible tube extends from the handle through the sheath. A tapered flexible extension is coupled to the flexible tube, the tapered flexible extension has a taper angle of between about 5 degrees and 15 degrees towards the handle. A bead of adhesive can be supplied at an end of the tapered flexible extension. A thrust block is coupled to the flexible tube, and an endoluminal prosthesis is positioned around the flexible tube between the thrust block and the tapered flexible extension with a space situated between the endoluminal prosthesis and the thrust block.

14 Claims, 4 Drawing Sheets

PROSTHESIS DEPLOYMENT SYSTEM

CROSS-REFERENCE TO RELATED APPLICATIONS

This application is related to and claims all benefit of U.S. Provisional Application Ser. No. 60/559,764 filed Apr. 6, 2004.

BACKGROUND OF THE INVENTION

1. Technical Field

This invention relates to a medical device and, in particular, a deployment system for a prosthesis that is adapted for implantation within the human or animal body for the repair of damaged vessels such as blood vessels.

2. Related Art

Throughout this specification the terms proximal and proximally with respect to a prosthesis deployment system refer to an end thereof nearest to a clinician. Similarly, distal and distally are intended to mean the end of the prosthesis deployment system that is farthest from the clinician.

The functional lumens of humans, such as blood vessels and ducts, occasionally weaken, or become blocked. For example, lumens in the biliary tree may be obstructed by malignant neoplasms, or may be narrowed by postoperative or other types of strictures. A common surgical intervention for occluded lumens is the use of a prosthesis to provide some or all of the functionality of the original, healthy lumen and/or preserve any remaining integrity by reinforcing a length of the existing lumen wall that spans the site of occlusion.

The deployment of intraluminal prostheses into the lumen of a patient from a remote location by the use of a deployment device or introducer has been disclosed in a number of earlier patents and patent applications. U.S. Pat. No. 4,562,596 entitled "Aortic Graft, Device and Method for Performing an Intraluminal Abdominal Aortic Aneurysm Repair" proposes the retention of a self expanding graft within a sleeve until it is to be deployed, at which time the sleeve is withdrawn and the graft is allowed to expand. These features and other features disclosed in U.S. Pat. No. 4,562,596 could be used with the present invention and the disclosure of U.S. Pat. No. 4,562,596 is herein incorporated by reference.

U.S. Pat. No. 4,665,918 entitled "Prosthesis System and Method" proposes a system and method for the deployment of a prosthesis in a blood vessel. The prosthesis is positioned between a delivery catheter and an outer sheath and expands outwardly upon removal of the sheath. These features and other features disclosed in U.S. Pat. No. 4,665,918 could be used with the present invention and the disclosure of U.S. Pat. No. 4,665,918 is herein incorporated by reference.

U.S. Pat. No. 4,580,568 entitled "Percutaneous Endovascular Stent and Method for Insertion Thereof" proposes a system and method for the deployment of a prosthesis in a lumen. The prosthesis is positioned between a delivery catheter and an outer sheath and expands outwardly upon removal of the sheath. These features and other features disclosed in U.S. Pat. No. 4,580,568 could be used with the present invention and the disclosure of U.S. Pat. No. 4,580,568 is herein incorporated by reference.

U.S. Pat. No. 4,950,227 entitled "Stent Delivery System" proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position. These features and other features disclosed in U.S. Pat. No. 4,950,227 could be used with the present invention and the disclosure of U.S. Pat. No. 4,950,227 is herein incorporated by reference.

U.S. Pat. No. 5,387,235 entitled "Expandable Transluminal Graft Prosthesis for Repair of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herein incorporated by reference.

U.S. Pat. No. 5,700,253 entitled "Flexible, Kink-Resistant, Introducer Sheath and Method of Manufacture" discloses apparatus and manufacturing methods for intraluminal deployment devices. These features and other features disclosed in U.S. Pat. No. 5,700,253 could be used with the present invention and the disclosure of U.S. Pat. No. 5,700,253 is herein incorporated by reference.

U.S. Pat. No. 5,720,776 entitled "Barb and Expandable Transluminal Graft Prosthesis for Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention and the disclosure of PCT Patent Publication Number No. WO03/034948 is herein incorporated by reference.

United States Published Patent Application No. 20030233140 entitled "Trigger Wire System" discloses release wire systems for the release of stent grafts retained on introducer devices. This feature and other features disclosed in United States Published Patent Application No. 20030233140 could be used with the present invention and the disclosure of United States Published Patent Application No. 20030233140 is herein incorporated by reference.

United States Published Patent Application No. 20040098079 entitled "Thoracic Aortic Stent Graft Deployment Device" discloses introducer devices adapted for deployment of stent grafts particularly in the thoracic arch. This feature and other features disclosed in United States Published Patent Application No. 20040098079 could be used with the present invention and the disclosure of United States Published Patent Application No. 20040098079 is herein incorporated by reference.

United States Published Patent Application No. 20040054396 entitled "Stent-Graft Fastening" discloses arrangements for fastening stents onto grafts particularly for exposed stents. This feature and other features disclosed in United States Published Patent Application No. 20040054396 could be used with the present invention and the disclosure of United States Published Patent Application No. 20040054396 is herein incorporated by reference.

PCT Patent Publication Number No. WO03/053287 entitled "Improving Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention and the disclosure of PCT Patent Publication Number No. WO03/053287 is herein incorporated by reference.

PCT Patent Publication Number No. WO98/53761 entitled "A Prosthesis and a Method and Means of Deploying a Prosthesis" discloses various embodiments of an introducer for positioning an expandable endovascular prosthesis in a lumen of a patient. This feature and other features disclosed in PCT Patent Publication Number No. WO98/53761 could be used with the present invention and the disclosure of PCT Patent Publication Number No. WO98/53761 is herein incorporated by reference.

One issue that arises with the use of an endoluminal prosthesis is that removal of the deployment system is preferably accomplished without disrupting the placement of the prosthesis. For example, any sharp or rough edge along a portion of a deployment system that passes through the endoluminal prosthesis during withdrawal of the deployment system may potentially catch on the prosthesis, thereby disrupting its placement. It would be desirable to provide a deployment system that has smooth edges along the portion thereof that passes through the endoluminal prosthesis during removal. Another issue that arises with the use of an endoluminal prosthesis is that the deployment system should provide tactile feedback to the clinician during placement of the endoluminal prosthesis. It would be further desirable to provide a deployment system that provides increased tactile feedback during prosthesis placement.

SUMMARY

A stent deployment system is provided that includes a handle and a flexible sheath coupled to the handle. The stent deployment system also includes a flexible tube that extends through the handle and outward from the sheath to a tapered flexible extension. The tapered flexible extension has a taper angle of between five degrees and fifteen degrees towards the handle. The stent deployment system can also include a bead of adhesive adjacent to an end of the tapered flexible extension.

The stent deployment system can further include a rigid tube coupled to the flexible tube, wherein the rigid tube extends from the handle to a hub. An endoluminal prosthesis may be positioned coaxial with the flexible tube. The endoluminal prosthesis can be self-expanding. A retaining tube can be coupled to an outer surface of the flexible sheath and extend from the flexible sheath partially to a location partially over the tapered flexible extension. A cylindrical sleeve can be coupled between the flexible tube and the tapered flexible extension.

A stent deployment system is also provided comprising a handle, a flexible sheath coupled to the handle, and a flexible tube that extends through the handle and through the sheath. A tapered flexible extension is coupled to the flexible tube. The tapered flexible extension has a taper angle of between five degrees and fifteen degrees towards the handle. A thrust block is coupled to and circumferentially surrounds the flexible tube. An endoluminal prosthesis is positioned coaxial with the flexible tube between the thrust block. and the tapered flexible extension. There is a space between the endoluminal prosthesis and the thrust block.

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
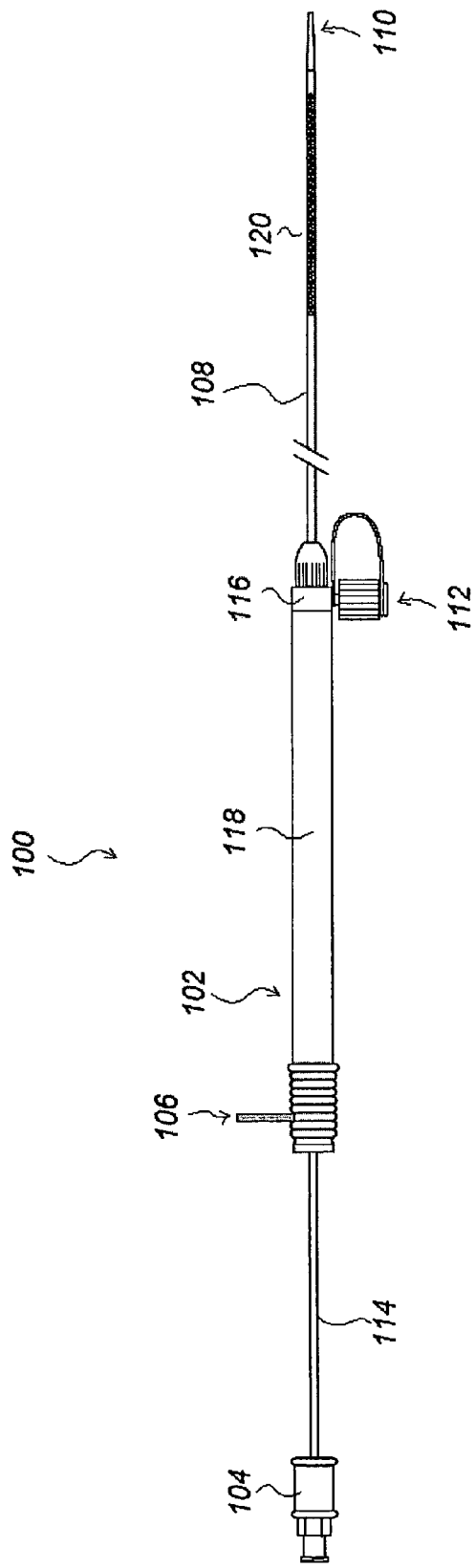
FIG. 1 is a side elevation view of a prosthesis deployment system with a prosthesis loaded therein.

FIG. 1 shows an endoluminal prosthesis 120 and an endovascular deployment system 100, also known as an introducer, for deploying the prosthesis 120 in a lumen of a patient during a medical procedure. The term "prosthesis" means any replacement for a body part or function of that body part. "Prosthesis" can also mean a device that enhances or adds functionality to a physiological system. The terms "endoluminal" and "intraluminal" describe objects that are found or can be placed inside a lumen in the human or animal body. A "lumen" can be an existing lumen or a lumen created by surgical intervention, including lumens such as blood vessels, parts of the gastrointestinal tract, ducts such as bile ducts, parts of the respiratory system, etc. "Endoluminal prosthesis" thus describes a prosthesis that can be placed inside one of these lumens.

The introducer 100 includes a handle 102, a lock 106, a flexible sheath 108, a tapered flexible extension 110, a rigid tube 114, and a hub 104. The handle 102 includes a handle body 118, a flushing port body 116, and a flushing port cap 112. During a medical procedure to deploy the prosthesis 120, the flexible sheath 108 and the tapered flexible extension 110 of the endovascular deployment system 100 will travel through a selected lumen to a desired deployment site. The handle 102 and the hub 104, which are acted upon by a clinician to manipulate the endovascular deployment system 100, remain outside of the patient throughout the procedure.

Figure 2:
FIG. 2 is a side elevation detail view of the prosthesis shown in FIG. 1.

The endoluminal prosthesis 120 is shown in greater detail in FIG. 2. The endoluminal prosthesis 120 can be a self-expanding stent that expands following its disengagement from the endovascular deployment system 100. Radiographic markers 122 can be attached to the endoluminal prosthesis 120 in order to aid in proper placement of the endoluminal prosthesis 120 in the lumen. For example, the radiographic markers 122 can be small rings or rivets of metal, such as stainless steel or gold.

Figure 3:
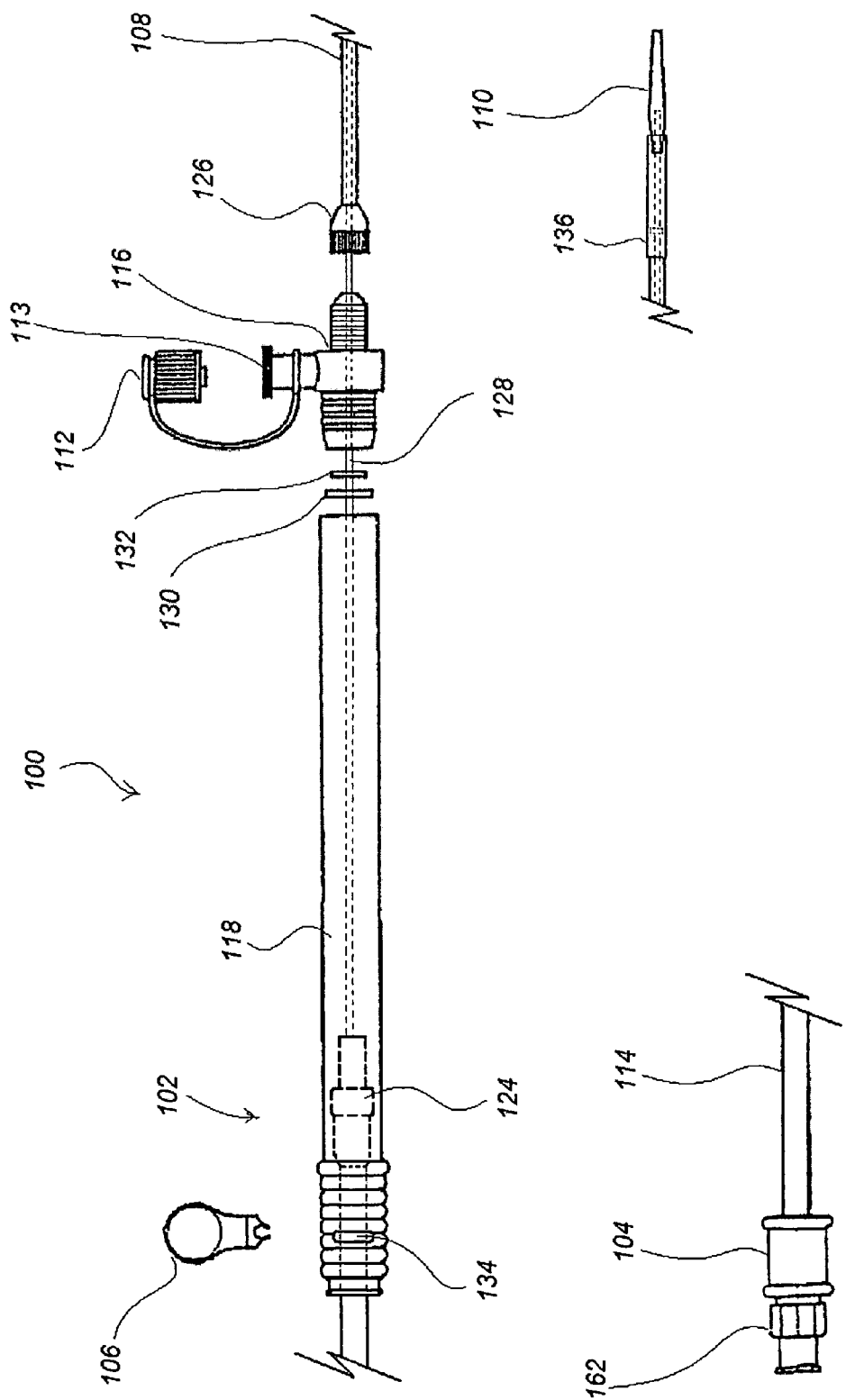
FIG. 3 is a partially exploded view of the prosthesis deployment system of FIG. 1.

A partially exploded view of the prosthesis deployment system 100 is shown in FIG. 3. A proximal port body 162 is coupled to the hub 104, which in turn is coupled to the rigid tube 114. The proximal port body 162, the hub 104, and the rigid tube 114 each contain an interior channel, the channels being in fluid communication with one another. The rigid tube 114 extends into the handle body 118. A stop 124 is coupled to the rigid tube 114 at a position inside the handle 118, which prevents the rigid tube 114 from being separated from the handle 118. The lock 106 is configured to be inserted in an aperture 134 of the handle 118. The rigid tube 114 can be extended from the handle 118 until the stop 124 is between the proximal end of the handle 118 and the aperture 134. With the rigid tube 114 in this position, the lock 106 can be placed in the aperture 134 and removably coupled to the rigid tube 114 to prevent inadvertent deployment of the endoluminal prosthesis 120.

The rigid tube 114 is coupled to a flexible tube 128. The flexible tube 128 has a channel therethrough in fluid communication with the channel on the interior of rigid tube 114. The flexible tube 128 extends out of the handle 118 through a disk 130, an o-ring 132, the flushing port body 116, a connector cap 126, the flexible sheath 108, and a retaining tube 136. The flushing port body 116 includes a flushing port 113, which is in fluid communication the channel in the flexible tube 128. The flushing port 113 can be used to flush the endovascular deployment system 100 prior to the medical procedure, and during the medical procedure as desired. The flushing port cap 112 can be removably coupled to the flushing port 113 to seal the flushing port 113. The flushing port body 116 is coupled to the distal end of the handle 118. The connector cap 126 is coupled to the flushing port body 116, and also coupled to the flexible sheath 108. Therefore, in operation, the flexible sheath 108 maintains a position relative to the handle 118, while the flexible tube 128 maintains a position relative to the rigid tube 114 and the hub 104. Thus, the flexible tube 128 can be moved relative to the flexible sheath 108 by changing the position of the hub 104 relative to the handle 118.

Figure 4:
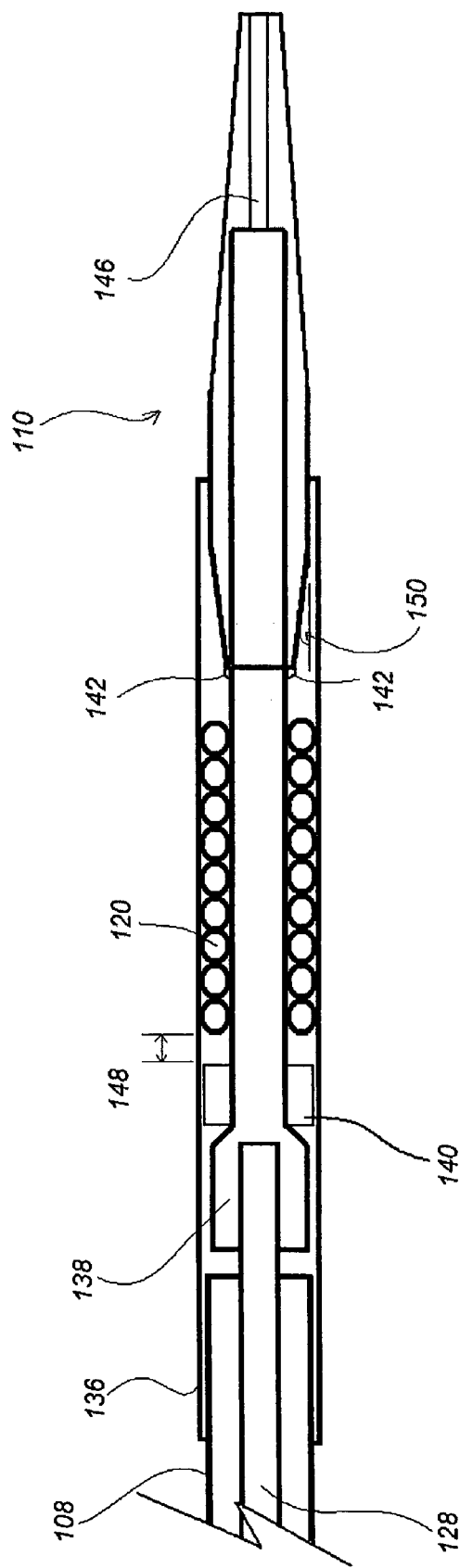
FIG. 4 is a schematic cross-sectional view of the distal end of the prosthesis deployment system and the prosthesis of FIG. 1 when the prosthesis deployment system is closed.

The flexible tube 128 extends to and is coupled to a cylindrical sleeve 138, shown in FIG. 4, which is coupled to the tapered flexible extension 110. The tapered flexible extension 110 has a channel therethrough, which is in fluid communication with the channel of the flexible tube 128 via a channel in the cylindrical sleeve 138, so that a continuous channel 146 exists in the endovascular deployment system 100 between the proximal end of the proximal port body 162 and the distal end of the tapered flexible extension 110. The continuous channel 146 through the endovascular deployment system 100 can be used to guide the deployment system 100 along an insertion wire (not shown) to a desired deployment site. Additionally, it may be desirable to supply a contrast agent to allow angiography to be performed during placement and deployment phases of the medical procedure. The proximal port body 162 is adapted to accept a syringe to facilitate the introduction of reagents into the continuous channel through the endovascular deployment system 100.

The retaining tube 136 is coupled to the flexible sheath 108, for example by an adhesive. The retaining tube 136 can be a heat shrink tube, which has diameter larger than the expanded diameter of the endoluminal prosthesis 120 prior to shrinking, so that the endoluminal prosthesis 120 can be compressed by shrinking the retaining tube 136 with a heater. Alternatively, the retaining tube 136 can have a diameter smaller than the expanded diameter of the endoluminal prosthesis 120, and the endoluminal prosthesis 120 can be held in a compressed state by a cylindrical tool during loading. The retaining tube 136 retains the endolumeal prosthesis 120 so long as the prosthesis deployment system 100 is in a closed position as shown in FIG. 4. The flexible tube 128 extends into the cylindrical sleeve 138. The cylindrical sleeve 138 is coupled to the flexible tube 128 to create a mounting section for the endoluminal prosthesis 120. The cylindrical sleeve 138 extends into and is coupled to the tapered flexible extension 110.

A thrust block 140 can be coupled to the cylindrical sleeve 138. The thrust block 140 can be a radiographic opaque marker, and can comprise a metal such as gold or platinum. Alternatively, the thrust block 140 can be radiographically transparent, and can comprise a polymer of high durometer. In either case, the thrust block 140 is preferably a ring or band that circumferentially surrounds the cylindrical sleeve 138, and has an outer diameter just slightly less than an inner diameter of the retaining tube 136. The flexible tube 128, the cylindrical sleeve 138, the thrust block 140, and the tapered flexible extension 110 move together as one piece when the hub 104 is locked to the handle 102 by the lock 106.

The retaining tube 136 is positioned coaxially around the flexible tube 128, the thrust block 140 and a portion of the cylindrical sleeve 138 when the prosthesis deployment system 100 is in the closed position. The flexible sheath 108 and the retaining tube 136 are coupled and move together as one, and can move relative to the flexible tube 128, the cylindrical sleeve 138, the thrust block 140, and the tapered flexible extension 110 when the lock 106 is removed from the aperture 134 in the handle 118. The retaining tube 136 extends from the flexible sheath 108 to cover a portion of the tapered flexible extension 110 when the prosthesis deployment system 100 is in the closed position.

The tapered flexible extension 110 has a proximal taper, and can have a distal taper. The proximal taper is at an angle 150 that is between about 5 degrees and 15 degrees, and is preferable between about 8 degrees and 12 degrees. The tapered flexible extension 110 has a maximum diameter that tapers down to about the diameter of the cylindrical sleeve 138. The distal taper can be between about 5 degrees and 30 degrees away from the handle. The distal taper and the proximal taper of the tapered flexible extension 110 can be created by grinding the tapered flexible extension 110 with a cylindrical grinding tool, or by heating and molding the respective end of the tapered flexible extension 110.

A bead of adhesive 142 can be applied adjacent to the proximal end of the tapered flexible extension 110 between the tapered flexible extension 110 and the cylindrical sleeve 138. For example, the bead of adhesive 142 can be a hardening or semi-hardening adhesive liquid or gel such as an epoxy, a glue, silicone, LOCTITE®, or some other similar substance. The bead of adhesive 142 may reduce any "sharpness" present in the transition from the tapered flexible extension 110 and the cylindrical sleeve 138.

The endoluminal prosthesis 120 is placed a longitudinal distance 148 away from the distal end of thrust block 140. The longitudinal distance 148 allows the clinician to feel the thrust block 140 make contact with the endoluminal prosthesis 120 shortly before the endoluminal prosthesis 120 prosthesis begins deployment. Without the longitudinal distance 148, the clinician would feel this contact as the endoluminal prosthesis 120 began deployment.

For example, because the endoluminal prosthesis 120 is self-expanding, there is a greater amount of friction between the endoluminal prosthesis 120 and the retaining tube 136 than between the endoluminal prosthesis 120 and the cylindrical sleeve 138. Therefore, when the cylindrical sleeve 138 and the thrust block 140 are "pushed" out of the retaining tube 136, the endoluminal prosthesis 120 has a tendency to remain motionless relative to the retaining tube 136. Pushing the hub 104 closer to the handle 102 allows the thrust block 140 to move relatively freely for the longitudinal distance 148, and allows the clinician to feel the contact between the thrust block 140 and the endoluminal prosthesis 120 before the endoluminal prosthesis 120 begins expanding as the prosthesis deployment system 100 transforms from the closed position shown in FIG. 4 to the open position shown in FIG. 5.

Figure 5:
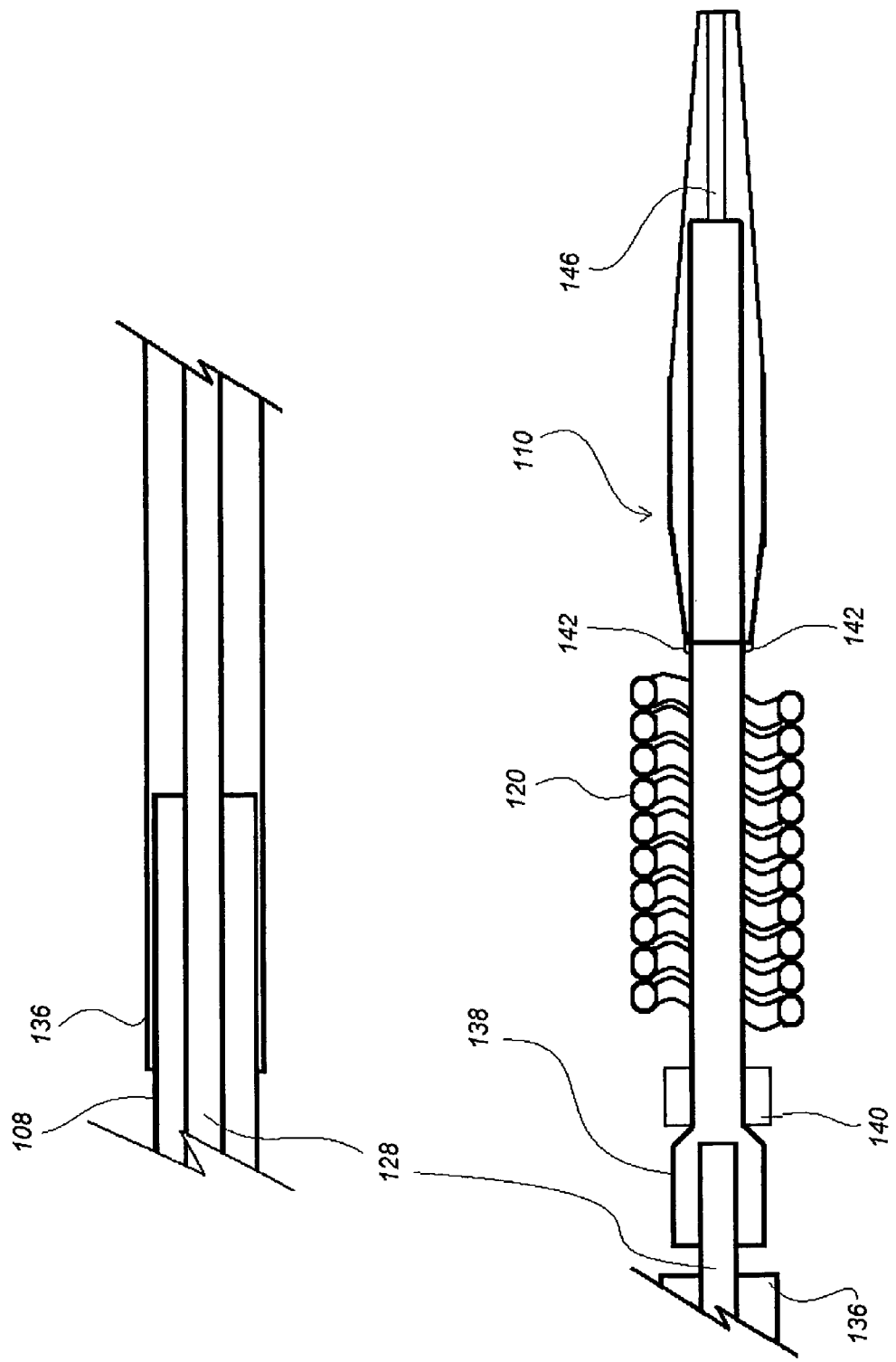
FIG. 5 is a schematic cross-sectional view of the distal end of the prosthesis deployment system and the prosthesis of FIG. 1 when the prosthesis deployment system is open.

In FIG. 5, the tapered flexible extension 110 is shown extended beyond the retaining tube 136. The endoluminal prosthesis 120 is shown expanded, because the retaining tube 136 is no longer holding the endoluminal prosthesis 120 in a compressed state. After the endoluminal prosthesis 120 has been deployed, as shown in FIG. 5, the tapered flexible extension 110 may be retracted back through the endoluminal prosthesis 120 until it is partially covered by the retaining tube 136 again. The proximal taper of the tapered flexible extension 110 can facilitate the retraction of the tapered flexible extension 110 through the deployed endoluminal prosthesis 120. The bead of adhesive 140 can further facilitate the retraction of the tapered flexible extension 110 through the deployed endoluminal prosthesis 120. Once the tapered flexible extension 110 is retracted at least partially inside the retaining tube 136, the prosthesis deployment system 100 may be withdrawn from the lumen, and removed from the patient.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A stent deployment system, comprising:
a handle,
a flexible sheath coupled to the handle,
a flexible tube extending into the handle and through the sheath about a longitudinal axis,
a tapered flexible extension coupled to the flexible tube, the tapered extension having a continuous reverse taper from a maximum diameter of the tapered flexible extension to an outer diameter of the flexible tube, the reverse taper facing toward the handle,
an endoluminal prosthesis disposed about the flexible tube, having a proximal end and a distal end, and
a distally advanceable thrust block coupled to and circumferentially surrounding the flexible tube, the thrust block disposed a longitudinal distance away from the proximal end of said prosthesis, providing tactile feedback to an operator when contact between the thrust block and said prosthesis is made after distal movement of the thrust block.

2. The system of claim 1 further comprising a retaining tube coupled to an outer surface of the flexible sheath and extending distally therefrom to the tapered flexible extension, wherein the thrust block has an outer diameter slightly less than an inner diameter of the retaining tube.

3. The system of claim 2 further comprising a closed position and an open position, the closed position being defined as the retaining tube coaxially disposed around the thrust block, said prosthesis, and a proximal portion of the tapered flexible extension, the open position being defined as the thrust block, said prosthesis, and said proximal portion of the tapered flexible extension located distal to a distal end of the retaining tube,
wherein, in the closed position, the thrust block is movable between a first position and a second position for contacting said prosthesis, the first and second positions being spaced from one another by said longitudinal distance.

4. The system of claim 1 further comprising a rigid tube coupled to the flexible tube, the rigid tube extending into the handle.

5. The system of claim 4 further comprising a hub coupled to the rigid tube.

6. A stent deployment system, comprising:
a handle,
a flexible sheath coupled to the handle,
a flexible tube extending from the handle and through the sheath about a longitudinal axis;
a tapered flexible extension coupled to the flexible tube, the tapered flexible extension having a transition to define a maximum diameter of the tapered flexible extension and a continuous reverse taper from the maximum diameter of the tapered flexible extension to an outer diameter of the flexible tube, where the reverse taper faces toward the handle and comprises an angle of between five degrees and fifteen degrees relative to the longitudinal axis,
a distally advanceable thrust block coupled to and circumferentially surrounding the flexible tube, and
an endoluminal prosthesis positioned coaxial with the flexible tube between the thrust block and the tapered flexible extension, said prosthesis spaced a longitudinal distance away from the thrust block, where the longitudinal distance is sufficient to provide tactile feedback to an operator when contact between the thrust block and said prosthesis is made after distal movement of the thrust block and before deployment of said prosthesis.

7. The system of claim 6 further comprising a bead of adhesive adapted to reduce sharpness in a transition between the tapered flexible extension and the flexible tube, the bead of adhesive disposed adjacent to a proximal end of the tapered flexible extension along the flexible tube.

8. The system of claim 6 further comprising a rigid tube coupled to the flexible tube, the rigid tube extending into the handle.

9. The system of claim 8 further comprising a hub coupled to the rigid tube.

10. The system of claim 6 further comprising a retaining tube coupled to an outer surface of the flexible sheath and extending distally therefrom to the tapered flexible extension.

11. The system of claim 10 wherein the retaining tube has an interior diameter greater than the maximum diameter of the tapered extension.

12. The system of claim 10 wherein said system has a closed position and an open position, the closed position defined as the retaining tube coaxially disposed around the thrust block, said prosthesis, and the tapered flexible extension, the open position defined as extension of the thrust block, said prosthesis and the tapered flexible extension past an end of the retaining tube.

13. The system of claim 6 wherein the tapered flexible extension includes a continuous forward taper facing away from the handle and disposed distal to the transition, the tapered flexible extension having a proximal end and a distal end and a smooth edges therebetween to provide a smooth edge along the entire tapered flexible extension to eliminate sharp or rough edges on the tapered flexible extension that are catchable on said prosthesis during withdrawal of said tapered flexible extension through said prosthesis.

14. The system of claim 6 wherein the tapered flexible extension has a forward taper facing away from the handle and comprising a second taper angle of between five degrees and thirty degrees relative to the longitudinal axis.

* * * * *